United States Patent
Grbic et al.

(10) Patent No.: US 10,335,115 B2
(45) Date of Patent: Jul. 2, 2019

(54) MULTI-VIEW, MULTI-SOURCE REGISTRATION OF MOVING ANATOMIES AND DEVICES

(71) Applicant: Siemens Healthcare GmbH, Erlangen (DE)

(72) Inventors: Sasa Grbic, Plainsboro, NJ (US); Tommaso Mansi, Plainsboro, NJ (US); Stefan Kluckner, Berlin (DE); Charles Henri Florin, Long Island City, NY (US); Terrence Chen, Princeton, NJ (US); Dorin Comaniciu, Princeton Junction, NJ (US)

(73) Assignee: Siemens Healthcare GmbH, Erlangen (DE)

(*) Notice: Subject to any disclaimer, the term of this patent is extended or adjusted under 35 U.S.C. 154(b) by 0 days.

(21) Appl. No.: 15/755,565

(22) PCT Filed: Sep. 3, 2015

(86) PCT No.: PCT/US2015/048214
§ 371 (c)(1),
(2) Date: Feb. 27, 2018

(87) PCT Pub. No.: WO2017/039663
PCT Pub. Date: Mar. 9, 2017

(65) Prior Publication Data
US 2018/0242946 A1 Aug. 30, 2018

(51) Int. Cl.
*A61B 8/08* (2006.01)
*A61B 8/00* (2006.01)
*G06T 7/33* (2017.01)
*G06T 7/73* (2017.01)
*G09B 23/28* (2006.01)

(52) U.S. Cl.
CPC .......... *A61B 8/0841* (2013.01); *A61B 8/4263* (2013.01); *A61B 8/5261* (2013.01);
(Continued)

(58) Field of Classification Search
CPC ... A61B 8/0841; A61B 8/4263; A61B 8/5261; A61B 8/58; G06T 7/33; G06T 7/75;
(Continued)

(56) References Cited

U.S. PATENT DOCUMENTS

2013/0237811 A1* 9/2013 Mihailescu ............ A61B 5/064
600/424
2014/0171799 A1 6/2014 Hershey et al.

FOREIGN PATENT DOCUMENTS

EP 2807978 12/2014

OTHER PUBLICATIONS

Ionasec et al, "Patient-Specific Modeling and Quantification of the Aortic and Mitral Valves From 4-D Cardiac CT and TEE", Sep. 2010, IEEE, vol. 29, No. 9, pp. 1636-1651 (Year: 2010).*
(Continued)

*Primary Examiner* — Edward Park

(57) ABSTRACT

Multi-source, multi-type image registration is provided. Images are received from a plurality of image devices, and images are received from a medical imaging device. A pre-existing diagram of a probe of the medical imaging device is received. A four-dimensional model is determined based on the received images from the image devices. A pose of the probe of the medical imaging device is determined based on the pre-existing diagram of the probe and the received images from the image devices. The plurality of images from the medical imaging device are registered with the four-dimensional model based on a common coordinate system and the determined pose of the probe.

20 Claims, 5 Drawing Sheets

(52) U.S. Cl.
CPC ................. *A61B 8/58* (2013.01); *G06T 7/33* (2017.01); *G06T 7/75* (2017.01); *G06T 2207/10016* (2013.01); *G06T 2207/10076* (2013.01); *G06T 2207/10136* (2013.01); *G09B 23/286* (2013.01)

(58) Field of Classification Search
CPC . G06T 2207/10016; G06T 2207/10076; G06T 2207/10136; G09B 23/286
See application file for complete search history.

(56) References Cited

OTHER PUBLICATIONS

International Search Report dated May 30, 2016 in corresponding International Application No. PCT/US2015/048214.
B. Curless and M. Levoy. A volumetric method for building complex models from range images. In SIGGRAPH 1996.
M. Okutomi and T. Kanade, A Multiple-Baseline Stereo, IEEE Trans. on Pattern Analysis and Machine Intelligence, 15(4):353-363 (1993).
R. Collins. A space-sweep approach to true multi-image matching. CVPR 1996.
Tobias Heimann, Peter Mountney, Matthias John, Razvan Ionasec: Real-time ultrasound transducer localization in fluoroscopy images by transfer learning from synthetic training data, Medical image analysis 2014.
Haralick, R. M., Joo, H., Lee, D., Zhuang, S., Vaidya, V. G., & Kim, M. B. (1989). Pose estimation from corresponding point data. Systems, Man and Cybernetics, IEEE Transactions on, 19(6), 1426-1446.

\* cited by examiner

54

52

50

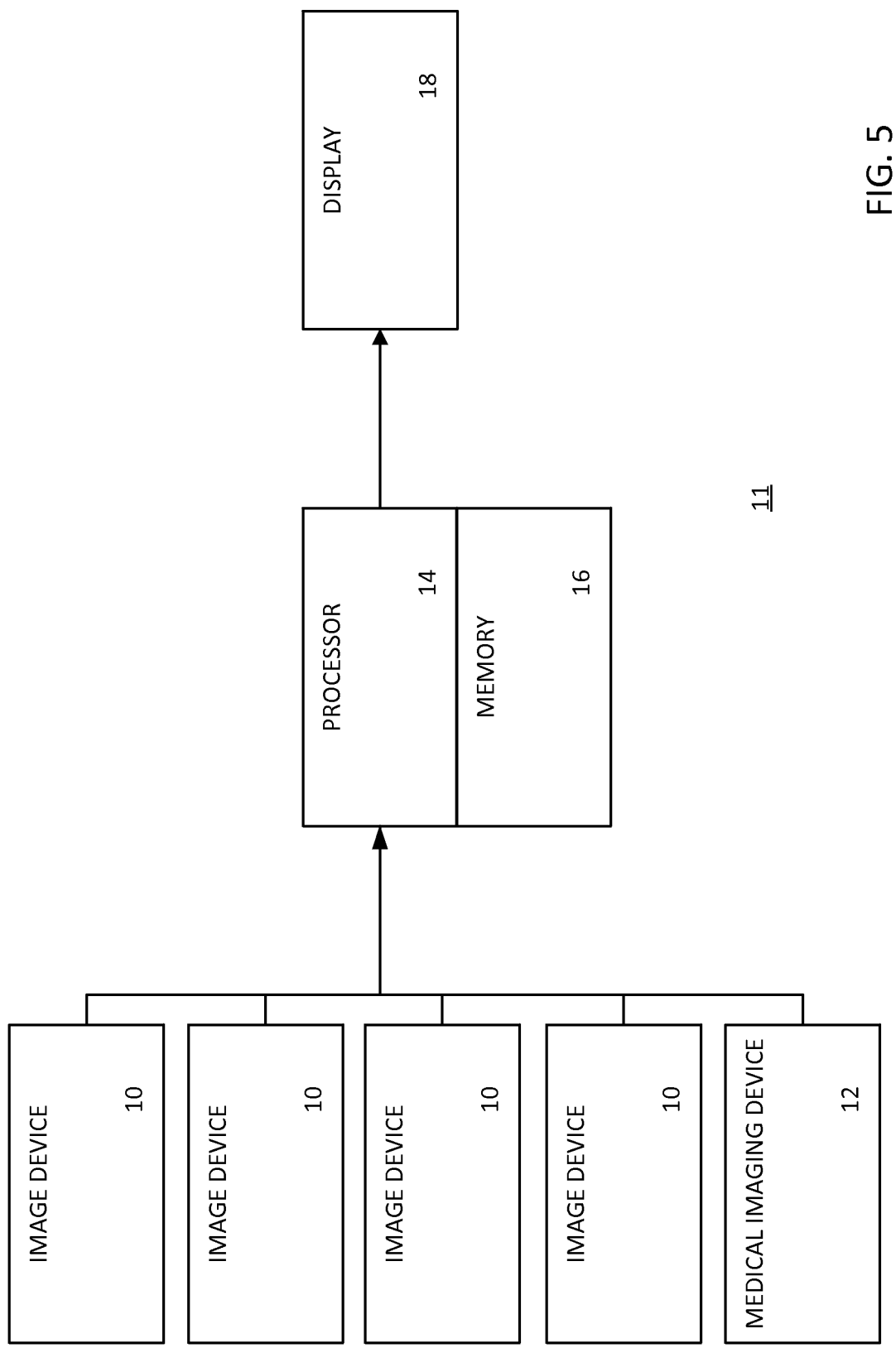

MULTI-VIEW, MULTI-SOURCE REGISTRATION OF MOVING ANATOMIES AND DEVICES

BACKGROUND

The following disclosure relates to medical imaging and, in particular, to registration of the moving anatomies and devices in spatial relationships within medical imaging devices.

In-vitro mechanical simulation is an important tool in product development, in testing of new medical devices, and in guiding improvements within the iterative product development cycle. Sensors, such as pressure sensors and flows sensors, are frequently used to collect data during in-vitro mechanical simulation testing phases. Medical imaging devices, such as ultrasound and computerized axial tomography (CT), are also used to collect data. Many cameras and scanners with high image resolution and extremely fine sampling capabilities (as compared to medical imaging devices) cannot be used in many medical applications where the tested device is located internal to a live subject. Some ultrasound scanners are limited to a maximum of sixty frames per second, while high resolution scanners may capture hundreds or thousands of frames per second.

Comprehensive evaluation of new medical devices in simulated environments may include testing with artificial anatomies. The interaction of a medical device with an artificial anatomy may be used to offer proof of concept from a computer simulation stage and/or to provide assessment of efficacy and long-term durability of a prototype. Accuracy and precision are desirable when analyzing information collected from the testing environment and medical device. Desired information may be associated with the interaction, changes, and cyclic movement of both artificial anatomy and the medical device in the testing environment. Drawbacks of gathering testing data with conventional medical imaging tools include limitations in image resolution and resolution of frame rate.

BRIEF SUMMARY

By way of introduction, the preferred embodiments described below include methods, computer readable media, and systems for data-based cycle estimation for multi-source, multi-type image registration. Images are acquired from multiple image devices and from a medical imaging device. The devices are arranged so as to capture imagery of in-vitro experiment set-up, which tests a prototype medical device with tissue or an anatomical model. The images also depict a probe of the medical imaging device. The images from the imaging device are used to create a four-dimensional model. The pose of the probe is determined based on a pre-existing diagram of the probe and the images from the image devices. The images from the medical image device are registered with the four-dimensional model based on a common coordinate system and the determined pose of the probe. Some or all of the four-dimensional model may be displayed in registration with portions of or all of the images from the medical imaging device, allowing four-dimensional registration of images captured from multiple devices and multiple sources.

In a first aspect, a method for multi-source, multi-type image registration is provided. The method includes receiving a plurality of camera images from a plurality of cameras, where the plurality of camera images depict a medical device being tested in an in-vitro experimental environment and the plurality of images further depicts a probe of an ultrasound scanner. The method also includes receiving a plurality of ultrasound images from an ultrasound scanner, where the plurality of ultrasound images depict at least a portion of the medical device in the in-vitro experimental environment. The method also includes receiving a pre-existing diagram of the probe of the ultrasound scanner, determining a four-dimensional model of at least a portion of the medical device being tested in the in-vitro experimental environment based on the received plurality of camera images, and determining a pose of the probe of the ultrasound scanner based on the pre-existing diagram of the probe and the received plurality of camera images. The method also includes registering the plurality of ultrasound images with the four-dimensional model based on a common coordinate system of the plurality of cameras and the determined pose of the probe.

In a second aspect, a system is provided for multi-source, multi-type image registration. The system includes a plurality of image devices, a medical imaging device, at least one processor; and at least one memory including computer program code for one or more programs; the at least one memory and the computer program code configured to, with the at least one processor. The system is caused to receive a plurality of images from the plurality of image devices; receive a plurality of images from the medical imaging device; and receive a pre-existing diagram of a probe of the medical imaging device. The system is further caused to determine a four-dimensional model based on the received plurality of images from the plurality of image devices and determine a pose of the probe of the medical imaging device based on the pre-existing diagram of the probe and the received plurality of the images from the plurality of image devices. The system is still further caused to register the plurality of images from the medical imaging device with the four-dimensional model based on a common coordinate system and the determined pose of the probe and display the four-dimensional model in registration with the plurality of images from the medical imaging device.

In a third aspect, a non-transitory computer readable storage medium having stored therein data representing instructions executable by a programmed processor for multi-source, multi-type image registration. The storage medium comprising instructions for receiving a plurality of images from a plurality of image devices; receiving a plurality of images from a medical imaging device; and receiving a pre-existing diagram of a probe of the medical imaging device. The storage medium further includes instructions for determining a four-dimensional model based on the received plurality of images from the plurality of image devices; determining a pose of the probe of the medical imaging device based on the pre-existing diagram of the probe and the received plurality of the images from the plurality of image devices; and registering the plurality of images from the medical imaging device with the four-dimensional model based on a common coordinate system and the determined pose of the probe. The storage medium further includes instructions for identifying a subject in the four-dimensional model; segmenting the subject from the four-dimensional model; identifying the subject in the plurality of images from the medical imaging device; and segmenting the subject from the plurality of images from the medical imaging device.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

FIG. 5 is a block diagram of one embodiment of a system of multi-source, multi-type image registration.

DETAILED DESCRIPTION OF THE DRAWINGS AND PRESENTLY PREFERRED EMBODIMENTS

Figure 1:
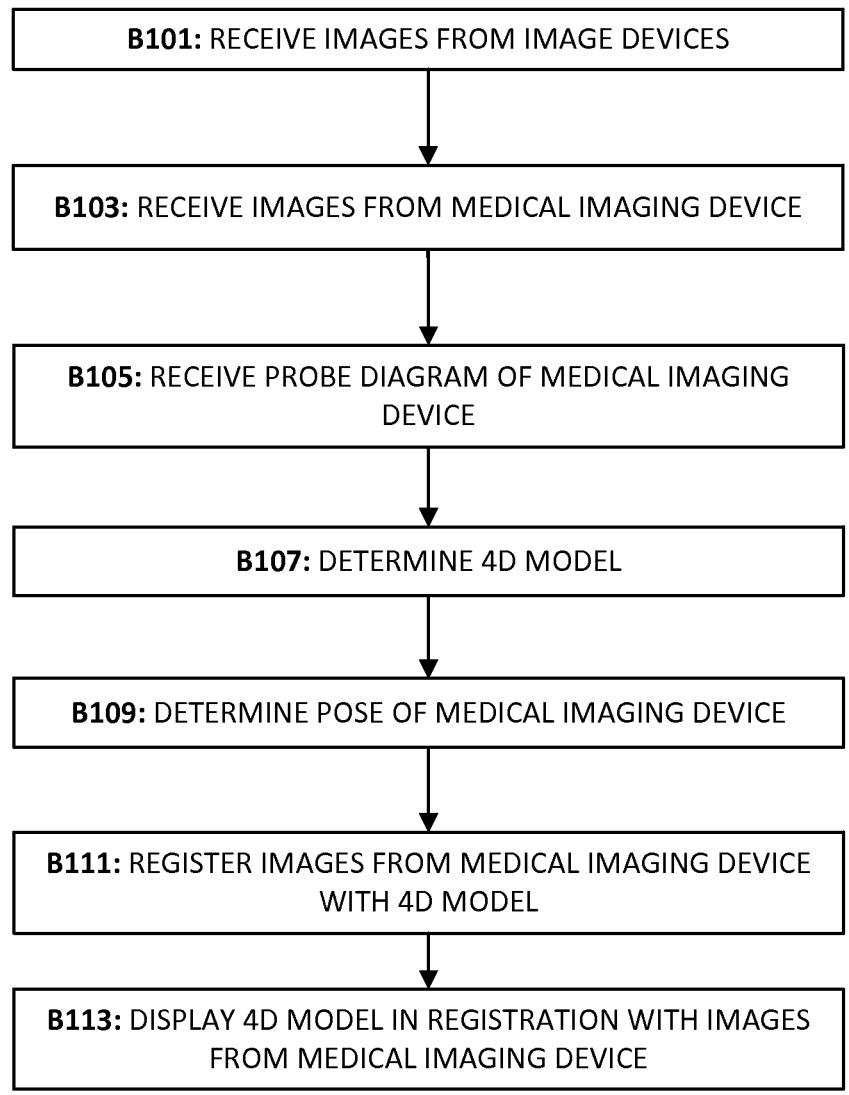
FIG. 1 is a flow chart diagram of one embodiment of a method of multi-source, multi-type image registration.

The system provides for the fusion of ultrasound or other medical imagery with imagery taken from high resolution cameras. The system includes a set of high resolution cameras with overlapping views focused in an in-vitro experimentation area. The system also includes a medical imaging device, such as an ultrasound scanner that is also focused on the in-vitro experimentation area. The probe of the medical ultrasound scanner is within view of at least one of the high resolution cameras. The in-vitro experimentation area may be used to test a variety of medical devices such as an implant or prosthetic device. The images acquired by the cameras and ultrasound may focus on visualizing the implant and any anatomical component models for the duration of testing. In order to create fused imagery, the ultrasound imagery is aligned with the camera imagery by detecting the ultrasound probe within the camera imagery. A four-dimensional model is reconstructed from the camera images, with the ultrasound imagery aligned and overlaid.

The system may be used to quantify the efficacy of medical devices in the course of in-vitro experimentation. The system may be used to calibrate, refine, or otherwise validate a medical imaging device. The system may be used to calibrate or refine the medical imaging device for a specific use case. Use cases may include testing environments for medical reconstruction or implantation associated moving anatomies such as the heart, lungs, or joints. The system provides the benefit of data collection from non-invasive medical imagery devices while leveraging the higher resolution image and the finer frame rate capabilities of other types of image capturing devices directly within an in-vitro experimentation context.

Some embodiments may be used for calibration or testing of medical imaging devices. In these embodiments, the high resolution imagery is used as a control for comparison to the images collected by the medical imaging devices. A medical imaging device, such as an ultrasound scanner, can be used with the subject technology in order to provide control imagery for a future implantation of a device in a patient. In one example of this use case, a medical device may be manufactured for a patient and customized to the needs and topography of the patient's body.

At a device testing stage in the context of patient-specific surgical planning, the system of the disclosure may be used to validate the operation of a medical device. For example, a control set of ultrasound images may be generated during device testing phases that may be used to anticipate and validate post-device implantation ultrasound images obtained from a live patient. The subject technology may be especially beneficial in cases of complex anatomical deformation, as in pediatric cases, where a personalized model may be highly desirable or necessary.

High resolution imaging during the device testing stage may be leveraged to provide additional certainty with the use of noninvasive medical imaging devices on the patient. For instance, a reconstructed mitral valve may designed for use with a human heart. Portions of a patient's heart may be modeled using a 3-D printed or silicon model and constructed to test the reconstructed mitral valve in-vitro. In this example, ultrasound imaging may be collected during the device testing stage to anticipate the expected ultrasound imaging upon surgical use of the reconstructed mitral valve. A benefit of the subject technology of multi-source, multi-type image reconstruction is assisting in anticipation of the inaccuracies present with current modalities of noninvasive imaging.

A further goal is to provide accurate geometrical information to assess experimental test data including the interaction of medical devices and anatomy in a test environment. It is contemplated that the provided system may be used in some applications with live subjects, such as the case with medical devices that are visible outside the body.

Figure 3:
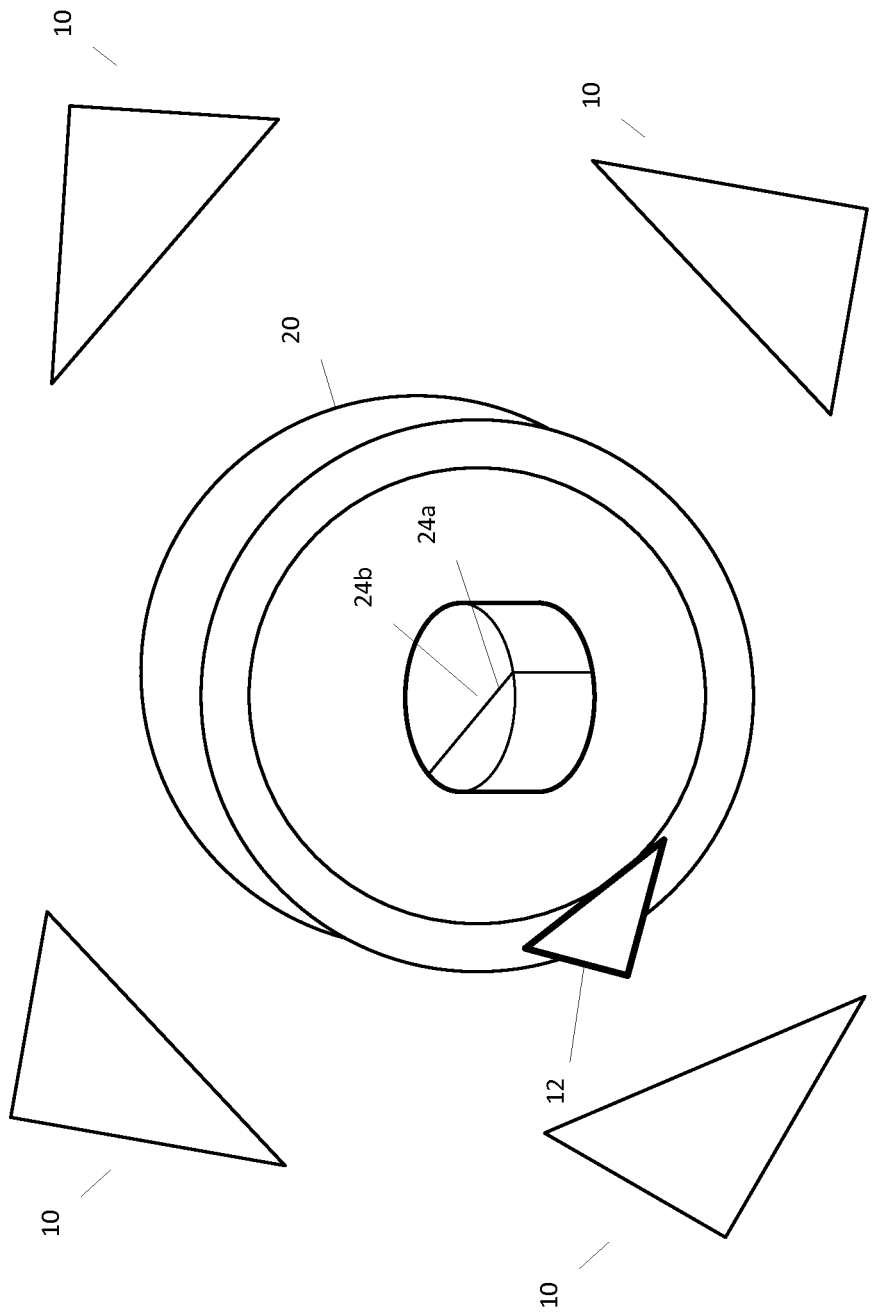
FIG. 3 is an illustration of an example system of multi-source, multi-type image registration.

FIG. 3 is an illustration of an example system of multi-source, multi-type image registration. The system is set up for the purposes of conducting an experiment within a test subject region, such as an in-vitro experimental set-up. The test subject 24*a-b* is located within a test subject area 20. The test subject area 20 may include a well or box in which the experiment will be conducted. Test subject area 20 may be a physical structure such that environmental parameters may be controlled or may be determined as the volumetric area that is captured by image devices 10. The physical structure of test subject area 20 may be composed of a translucent material, such as acrylic, for the purposes of preventing obstruction to image devices 20.

Test subject area 24*a-b* may include a physical instrument 24*a* and an anatomy model 24*b*. Validation of the physical instrument 24*a* may be a goal of the experiment. In one non-limiting example, physical instrument 24*a* may be a heart valve replacement device, and anatomy model 24*b* may be an artificial model of portions of a heart. A goal of experimentation for this non-limiting example may be to determine whether leakage occurs as the modeled heart beats with the replacement device. Physical instrument 24*a* and anatomy model 24*b* are contemplated to be any instrument or model and are not limited to instruments and models designed for human use and are not limited to experimentation settings for the purpose of medical applications. Test subject area 20 may include only a physical instrument 24*a* or may include only an anatomy model 24*b*. Physical instrument 24*a* and anatomy model 24*b* may be constructed of any material and may be assembled, machined, 3D printed, grown, molded, or constructed in any other manner. Anatomy model 24*b* may include valves, tubes, pipes, or other devices designed to mimic parts, volumes, and/or functions of the human body. Anatomy model 24b may include water, saline, glycerine solutions, blood, plasma or other fluids.

Quantitative data assessing the size, placement, duration, pressure or other conditions associated with any device failures may be sought through experimentation on the test subject 24. Assessment of the changes in device 24a geometries in an anatomical setting 24b may be a goal of experimentation. Specific inquiries such as determination of how far a replacement heart valve device 24a opens once attached to an anatomic model 24b may be accurately determined. The purpose of experimentation using the system may be to observe or accurately quantify variations in the device operation over anatomical movement cycles. Effects on the anatomical system may also be measured precisely and accurately during the operation and/or failure of the device.

Image devices 10 are placed around a test subject area in which one or more experiments will be conducted. The orientation and pose of each camera is such that it may capture a view of the test subject area 20 that overlaps with the view of at least one other image device 10 in the system. Any number of image devices 10 may be used, so long as the view of the image devices maintains overlap sufficiently to estimate a three-dimensional depth model. The number, pose, and orientation of the cameras may be dictated by size and layout of the test subject area 20 and may be optimized or refined during a calibration process of the image devices 10. Medical imaging device 12 is placed such that the device or a probe of the device is in view of at least one image device 10. A sensor or probe of medical imaging device 12 may be placed in view of an image device 10 while other portions of the medical imaging device may be outside the view of image devices 10. The probe or the medical imaging device itself may be affixed to a structure of test subject area 20 or may be contained entirely within test subject area 20. Image devices 10 and medical imaging device 12 correspond to similarly labeled system components of FIG. 5.

In alternative or additional embodiments, the volumes or images of the four-dimensional camera model of the in-vitro testing environment registered with the images from the medical imaging device are used for quantification. A volume, area, length, curvature, flow, pressure, delta (i.e., change) value or other quantity is calculated. Additional processing may be conducted to enhance the visualization including image processing designed to smooth, highlight, or otherwise enhance the imagery.

FIG. 1 is a flow chart diagram of one embodiment of a method of multi-source, multi-type image registration. FIG. 1 is described with respect of system components illustrated in FIG. 3 and FIG. 5.

The acts are performed in the order shown or different orders. For example, blocks B101, B103 and B105 are performed in any order and at any time prior to use of the data in one of the other acts. Additional, different, or fewer acts may be provided. For example, acts for user interaction are added. As another example, act B113 is not performed.

In block B101, images are received by processor 14 from multiple image devices 10 and may depict a medical device, prosthetic, implant, or physical implement 24a being tested in an experimental environment 20, such as an in-vitro environment. The images may also depict anatomical model 24b interacting with the environment and/or part of the experimental environment 20. The images may be two-dimensional images. The image devices 10 may include still cameras, video cameras, or scanners. In block B103, images are received by processor 14 from a medical imaging device 12. The images received may be in the form of real-time ultrasound imagery reconstructed by the ultrasound scanner. The medical imaging device 12 may be focused on a portion of the experimental environment and thus, may depict a portion of the same view as captured by images received from the multiple image devices 10. The probe of the medical imaging device 12 appears in the view of at least one image device 10. The medical imaging device may be an ultrasound scanner or CT scanner and may be capable of capturing four-dimensional imagery. Image capture from image devices 10 and from medical imaging device 12 are captured at the same time or substantially the same time. Substantially accounts for differences in frame rate and/or differences in starting/ending time during an image capture of the same experiment or event. The frame rate (i.e., number of frames per second) may be substantially greater from the image device 10 than the medical device 12. Substantially greater is by a factor of two or more. The images received from image devices 10 and medical image device 12 are captured during the course of conducting an experiment in the in-vitro test subject region. The image capture may last the duration of the experiment. The duration of the experiment may be on the scale of milliseconds or may extend for days, weeks, or months. The rate of image acquisition from the image devices 10 and the medical image device 12 may be specified by the user at the beginning of the experiment or may be adjusted throughout the course of experimentation. Image capture may be specified to occur for a subset of time of the duration of the experiment.

In block B105, a pre-existing diagram of a probe of the medical imaging device 12 is received by processor 14. The pre-existing diagram for the probe and/or entire medical image device 12 may be provided by manufacturer of the medical imaging device 12. Alternatively, a three-dimensional model of the salient portion of the medical imaging device (such as the portion of the medical imaging device within the test subject area) may be obtained using the network of image devices 10 or a different image device network in advance of set-up and commencement of an experiment. The pre-existing diagram may be a vector diagram, a schematic, a computer aided design (CAD) file, a stereolithography (STL) file, three-dimensional model, mesh, boundary model, or other data set sufficient to establish either a two-dimensional outline or three-dimensional surface geometry of at least part of the medical imaging device 12.

In block B107, a four-dimensional model of the area depicted by image devices 10 is determined by processor 14 based on the received images from the multiple image devices 10. The four-dimensional model is determined based on the overlapping viewpoints of the network of image devices 10. The four-dimensional model is constructed from an estimated three-dimensional depth map fused into a canonical coordinate system from individual two-dimensional image captures at individual time stamps.

An initial calibration process for the image devices 10 may be performed in advance of experimentation in order to provide parameters used during the determination of the four-dimensional model. Calibration of the network of image devices 10 may include image captures using a model or image in the test subject region with known values, such as a checkerboard pattern. Each camera may be identified based on the captured images during the calibration process and the image devices 10 may then be identified in accordance with a coordinate system common to all image devices 10 in the network. Camera information including pose, focal length, orientation, and location regarding each image device 10 are known or determined during the calibration process. Following the calibration process, the four-dimensional model may be determined through reconstruction of discrete captured images from the network calibrated image devices 10 on a pixel by pixel or voxel by voxel basis through projected camera views, feature extraction or other techniques.

In one embodiment, the process of determining the four-dimensional model includes first estimating a three-dimensional depth model by correlating projected image device views with a reference view, pixel by pixel for each two-dimensional image capture. Multiple-baseline stereo matching may be used in this embodiment to create the three-dimensional depth model by systematically comparing pairs of images by the image devices 10 for each point in time and combining the results of each pair until all views of the network of image devices 10 are considered. Preferably, the reference view is selected as a view of the test subject that is free of occlusions. For each paired image, the distance between cameras (baseline) is known along with the focal length of each image device 10. Disparities between images are determined, and depth of test subjects within the area is estimated. The three-dimensional depth model may be determined using sum of squared-difference values, sum of absolute differences, cross correlation, or other techniques.

Some embodiments may employ feature detection for construction of the three-dimensional depth model. Corner or edge features may be detected in individual two-dimensional image captures from the image devices 10. The three-dimensional depth model is constructed using a space-sweep method to determine the three-dimensional location of the detected features. The test subject area may be divided into voxels, and a plane may be swept through the space over a projection of each captured image over the established volume to determine the three-dimensional depth model. This process is repeated for each set of images at each point in time to generate the four-dimensional model.

The three-dimensional depth model is constructed for each point in time creating a time based four-dimensional model. Each individual three-dimensional depth model may be determined based only on images captured at the same point in time. The individual three-dimensional depth models are organized in a canonical coordinate system creating the four-dimensional model. In some embodiments, the four-dimensional model may represent only portions of the test subject area and may be segmented manually, semi-automatically, or fully-automatically. An automatically or manually drawn region of interest (ROI) may be segmented before, after, or during the creation of the four-dimensional model. Segmentation of images in advance of determination of the four-dimensional model may increase computational efficiency.

In block B109, a pose of the probe of the medical imaging device 12 is determined by processor 14 based on the pre-existing diagram of the probe and the images from the image devices 10. In preferred embodiments, the probe of the medical imaging device 12 is rigid or assumed to be rigid. However, some portions of the probe (such as portions of the cord or handle) need not be rigid. In some embodiments, the probe may exhibit deformation based on a semi-rigid material without any significant error in registration. Pose estimation may be determined from a subset of the captured images from image devices 10.

Pose estimation may be determined as a translation and orientation parameter of a rigid-transformation. The pre-existing diagram (i.e., template model of probe or medical imaging device 12) is mapped to the captured two-dimensional images from image devices 10. Correlation may be used to locate the probe in the image while also determining the pose. Methods of feature extraction may be used to determine the pose in captured images. Machine learning algorithms may further be used to train and create a classifier for the probe for increased accuracy in pose estimation.

In block B111, images from the medical imaging device 12 are registered by processor 14 with the four-dimensional model based on a common coordinate system and the determined pose of the probe. The pose of the probe of the medical device 12 may be determined based on the translation and orientation parameters of a transformation matching the pre-existing diagram of the probe to the captured image data from the test subject region. Because geometric and size characteristics of the probe are known, correlation between the probe and the images captured by the medical image device 12 may be mapped within the test subject region accurately. Once the location of the probe is known in the coordinate system associated with the image devices 10, the images captured by the medical image device 12 may be projected onto the four-dimensional model using the same coordinate system.

In block B113, the four-dimensional model is displayed on display 18 in registration with the images from the medical imaging device 12. The display 18 provides a visualization of the four-dimensional model in registration with four-dimensional medical imagery. The visualization may be rendered using volume rendering techniques (VRT), multi-planar reconstruction (MPR), or other rendering technique. The images of the medical imaging device may constitute a second four-dimensional model that may be displayed as an overlay on the four-dimensional model created from the image devices 10.

In some embodiments, portions of the four-dimensional model or ultrasound may be color-coded, such as displaying simulated blood flow in another color so that the flow path may be easily identified. In some embodiments, the resulting visualization may be displayed in real time, slow motion, or fast motion.

The visualization may be used to calibrate the medical imaging device 12 based on the plurality of images from the medical imaging device 12 that are registered with the four-dimensional model. The calibration of medical imaging device 12 may optimize the image capturing capabilities of the device by optimizing spatial resolution and reducing noise. The higher resolution image devices 10 serve to provide control data for comparison with the medical imaging device data. In one non-limiting application, the test subject is an anatomy model 24a of thin leaflets, such as the primary leaflets of the heart's mitral valve. In this example, four-dimensional ultrasound scanner may serve as the medical imaging device 12. Ultrasound imagery and high resolution imagery are taken of the a mitral valve model constructed in an in-vitro setting. The two sets of imagery may be compared with high resolution camera imagery of the anatomy model 24a. The comparison may then be used to calibrate or fine tune settings of the ultrasound scanner in order to obtain more accurate visualization for use with thin leaflets.

In another example, the experiment may include refining the placement of the ultrasound probe (or other medical imaging device 12) with respect to an anatomy model 24a and/or physical implement 24b by comparison of ultrasound imagery to high resolution camera imagery by obtaining imagery with the medical imaging device 12 in multiple locations with respect to the test subject.

Figure 2:
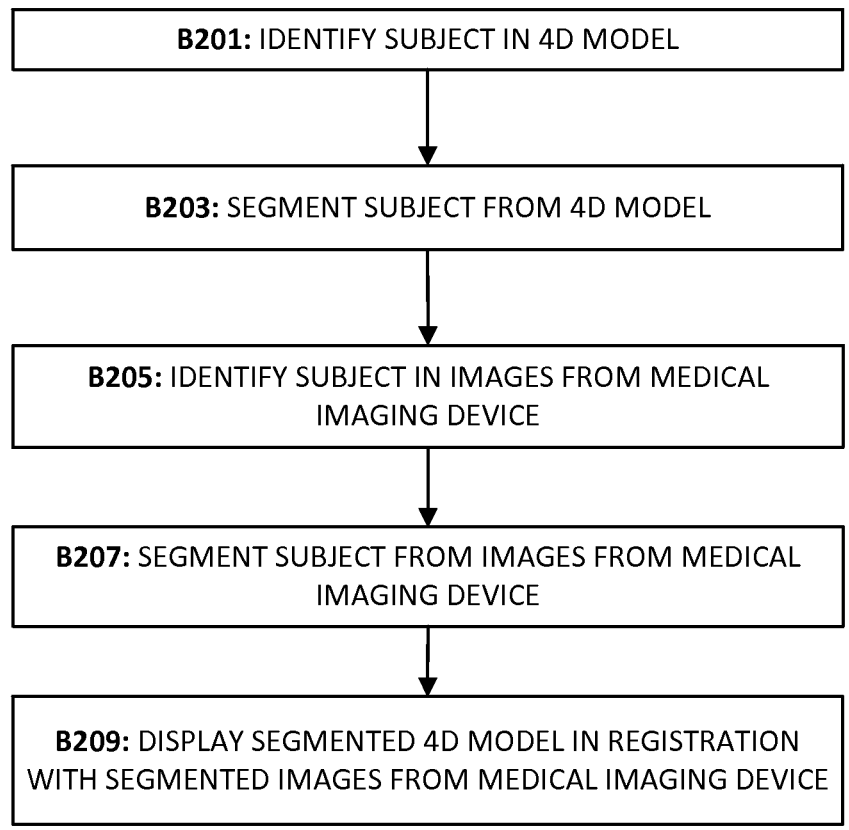
FIG. 2 is a flow chart diagram in accordance with another embodiment of a method of multi-source, multi-type image registration.

FIG. 2 is a flow chart diagram in accordance with another embodiment of a method of multi-source, multi-type image registration. In some embodiments, only a portion of the test subject or a selected time frame during the experiment are to be viewed and/or analyzed. FIG. 2 is described with respect to system components illustrated in FIG. 3 and FIG. 5.

The acts are performed in the order shown or in different orders. For example, blocks B205 and B207 may performed before, after, or during the other acts. Additional, different, or fewer acts may be provided. For example, acts for user interaction are added. As another example, acts B205 and B207 are not performed.

In block B201, a subject or area is identified in the four-dimensional model. The subject or area may be identified via manual user selection at a workstation connected to the processor 14, memory 16, and display 18 of FIG. 5. A boundary may be drawn or selected based on the four-dimensional model displayed. The selected area may be alternatively identified by specifying a window of interest. Alternatively, processor 14 identifies the subject or area. The identified subject or area may be a portion of the test subject 24a (a physical instrument) and/or 24b (an anatomy model) or a region of the test subject area 20. The subject is segmented from the four-dimensional model in block B203. The subject may be segmented by processor 14 using cropping, thresholding, edge detection, feature extraction or other image processing techniques.

In block B205, the same subject is identified in images from the medical imaging device 12. In block B207, the subject is segmented from images from the medical imaging device 12. A boundary may be drawn or selected based on the images from medical imaging device 12 that are displayed. The selected area may be alternatively identified by specifying a window or region of interest. Alternatively, processor 14 identifies the subject or area. The subject may be segmented by processor 14 using cropping, thresholding, edge detection, feature extraction or other image processing techniques. The segmented subject from the four-dimensional model is displayed in display 18 in registration with the segmented subject from the plurality of images in block B209. The segmented visualization may be played as a movie with four-dimensional ultrasound imagery overlaid on the four-dimensional model.

In some embodiments, areas of the resulting visualization (the four-dimensional model in registration with the images from the medical imaging device) may be extracted from the registered scene manually, semi-automatically, or fully automatically. Delineation of a subject or area of interest may be conducted by identification and segmentation of the area of interest from each captured image of the medical image device 12 and/or from identification and segmentation of the captured images or frames from the image devices 10. In one non-limiting example, the area of segmentation may be of the seal between the heart valve replacement (physical implement 24a) and the physical model of the heart (anatomical model 24b).

The segmentation may be a cross-section across the volume, or may be multi-planar views. Segmentation of the visualization may include segmentation in the time dimension. Selection of one or more cardiac cycles, breath cycles, or other periodic events may constitute the selected subject. Identification and segmentation of a specific event within a cycle may also be provided. Selection of temporally discrete portions of the visualization may be concatenated and visualized as a movie with only the selected frames.

In an alternate embodiment, the subject may be identified and segmented from only one of the image source types (i.e., from only the four-dimensional model derived from image devices 10 or from only the collected data from the medical imaging device 12) and displayed in registration with the entire reconstructed image from the other type of image capture device. For example, the four-dimensional model may be segmented or cropped so that only the physical implement 24a is displayed from the four-dimensional model in registration with the uncropped set of images from the medical imaging device 12.

Figure 4:
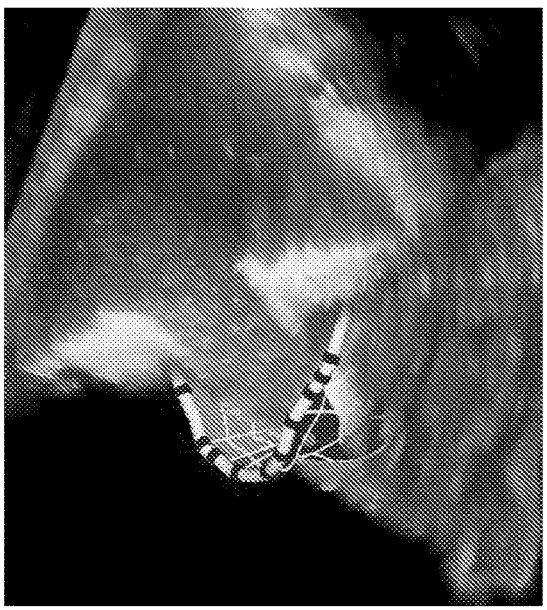
FIG. 4 illustrates an example of registered images using a system of multi-source, multi-type image registration.
Figure 4:
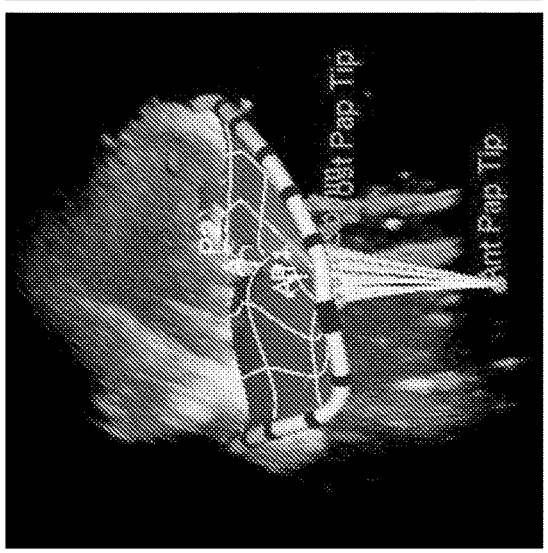
Figure 4:
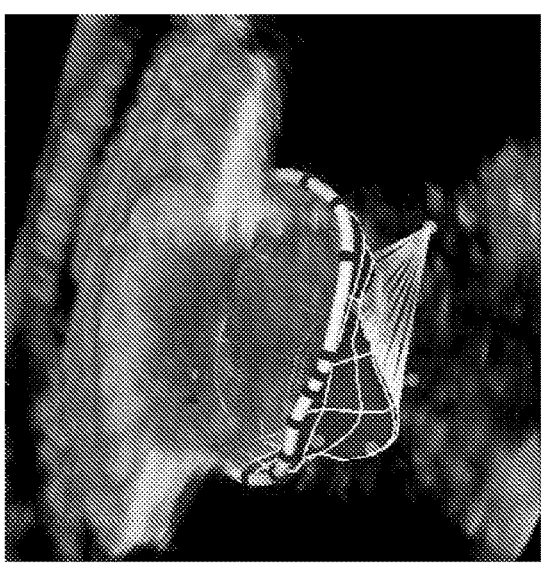

FIG. 4 illustrates an example of images 50, 52, and 54 which illustrate still images comporting with one embodiment in accordance with the method of multi-source, multi-type registration. The exemplary images illustrate a reconstructed mitral valve mechanical device aligned with an ultrasound image depicting an anatomical model in an in-vitro experiment that and may be used to determine efficacy of the device and quantify any failures of the device. The reconstructed mitral valve is mounted on a portion of a cadaver heart shown in ultrasound images.

FIG. 5 shows a system of multi-source, multi-type image registration. The system 11 includes image devices 10, a medical imaging device 12, a processor 14, a memory 16, and a display 18. The processor 14 and the memory 16 and display may be a computer or workstation apart from the image devices 10 and medical imaging device 12. In other embodiments, the processor 14 and/or memory 16 are part of one or more of the image devices 10 and/or medical imaging device 12. In alternative embodiments, the system 11 is a workstation, computer, or server for multi-source, multi-type image registration that additionally includes data acquired by a separate system in real-time and/or additionally includes previously acquired patient-specific data stored in a memory.

Additional, different, or fewer components may be used. For example, a user interface may be provided for entering an ROI, rotating the view of the four-dimensional model, calibration of the system 11, calibration of the medical imaging device 12, selection of duration, selection of frames per second, or selection of other parameters during the experiment period or configuring rendering.

The computing components of the system, such as the image devices 10, the medical imaging device 12 and/or the processor 14 are configured by hardware, software, firmware, and/or circuit design to perform calculations or other acts. The computing components operate independently or in conjunction with each other to perform any given act, such as the acts of FIGS. 1-2 or other acts associated with the method. The acts are performed by one of the computer components, another of the computing components, or a combination of the computing components. Other components may be used by the computing components to scan or perform other functions.

The image devices 10 are any still camera, video camera, charge coupled device (CCD) camera, range scanner, or any known or later developed device that may facilitate the capture of an image or data that may be representative of an image. The medical imaging device 12 is any now known or later developed medical imaging device including, but not limited to an ultrasound scanner or CT system. The raw data from the image devices 10 may be reconstructed into pixel or voxel values representing overlapping images of the test subject region. The image devices 10 are used to provide a four-dimensional reconstruction of the test subject region. The image devices 10 may be described as a network of image devices. The image devices 10 may communicate with each other via a wired or wireless network and/or may be in communication with a common processor memory, such as processor 14 and memory 16.

The medical imaging device 12 may include a processor, such as the processor 14 or other processor, for reconstructing a sequence of two-dimensional images over time. The raw data from the scanning is reconstructed into pixel or voxel values representing attenuation or other x-ray characteristics at different locations or points in the test subject region. The medical imaging device 12 provides another reconstruction from projection data of the test subject region. Medical imaging device 12 may produce images in two, three, or four dimensions.

The processor 14 is a general processor, digital signal processor, three-dimensional data processor, graphics processing unit, application specific integrated circuit, field programmable gate array, digital circuit, analog circuit, combinations thereof, or other now known or later developed device for processing medical data. The processor 14 is a single device, a plurality of devices, or a network. For more than one device, parallel or sequential division of processing may be used. Different devices making up the processor 14 may perform different functions, such as determining position and orientation by one processor, segmenting an image by one processor, and rendering by another processor. In one embodiment, the processor 14 is a control processor or other processor of one or more of image devices 10 and/or medical imaging device 12. The processor 14 operates pursuant to stored instructions to perform various acts described herein, such as acts of FIGS. 1 and 2.

The processor 14 is configured to determine a four-dimensional model based on the received images from the image devices 10. The processor may determine a common coordinate system from a calibration process of the image devices 10. The processor 14 may be configured to identify and segment an ROI from collected image data, which may include segmentation of the medical imaging device 12, a probe of the medical imaging device 12, or the test subject area or a portion thereof.

The processor 14 is configured to determine a pose of medical imaging device 12 or a probe of the medical imaging device 12. The processor 14 is configured to determine a common coordinate system amongst the pre-existing probe or medical device diagram and the collected images. The processor 14 is configured to establish a common coordinate system amongst the collected image data from the medical imaging device 12 and the image devices 10.

The processor 14 is configured to render an image or sequence of images from the test subject area over time. Surface or projection rendering may be performed. A multi-planar reconstruction may be created from the ultrasound or camera images over time by processor 14. Where formed images are provided for a single plane, then a sequence of two-dimensional images are provided.

The display 18 is a cathode ray tube (CRT), liquid crystal display (LCD), plasma, projector, printer, or other output device for showing an image. The display 18 displays an image or sequence of images of the four-dimensional model registered with the images from the medical imaging device. A segmented portion of a probe of the medical device 12, a pre-existing diagram of a probe of the medical imaging device 12, a segmented portion of the test subject area, or data associated with an experiment conducted in the test subject area or a calibration of medical device 12 or of system 11 may be displayed on display 18. A single image from an individual image device 10 or medical imaging device 12 may be alternatively or additionally displayed. A multi-planar reconstruction or volume rendering of a selected sequence of the experiment may displayed. A sequence of images may be displayed as a video.

In one embodiment, the display 18 is configured to display the four-dimensional model in registration with the medical device images. The display 18 may additionally display data collected or analyzed regarding the test subject. The displayed image may include a sequence of images or movie showing the movement and performance of the test subject.

The memory 16 is a buffer, cache, RAM, removable media, hard drive, magnetic, optical, database, or other now known or later developed memory. The memory 16 is a single device or group of two or more devices. The memory 16 is within the system 11, part of a computer with the processor 14, or is outside or remote from other components.

The memory 16 stores the data representing the test subject area. The data includes raw data, such as projection or image data from image devices 10 and medical imaging device 12. The data may be reconstructed medical device images or a reconstruction of image devices 10. The data may be a registered reconstruction of the medical device images and image device images in a whole or segmented representation. The data represents a three-dimensional region. Any format may be used, such as voxels interpolated to a three-dimensional grid or data representing parallel or non-parallel planes. The data may be segmented, such as including locations known to be for different areas in the test subject area or in relation to a patient anatomy. The memory 16 may store any of the data accumulated or measured during the experiment.

The memory 16 is additionally or alternatively a non-transitory computer readable storage medium with processing instructions. The memory 16 stores data representing instructions executable by the programmed processor 14 for data-based cycle estimation of multi-source, multi-type image registration. The instructions for implementing the processes, methods and/or techniques discussed herein are provided on computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing and the like.

In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

While the invention has been described above by reference to various embodiments, it should be understood that many changes and modifications can be made without departing from the scope of the invention. It is therefore intended that the foregoing detailed description be regarded as illustrative rather than limiting and that it be understood that it is the following claims, including all equivalents, that are intended to define the spirit and scope of this invention.

We claim:

1. A method of multi-source, multi-type image registration:
   receiving a plurality of camera images from a plurality of cameras, wherein the plurality of camera images depict a medical device being tested in an in-vitro experimental environment and wherein the plurality of images further depicts a probe of an ultrasound scanner;
   receiving a plurality of ultrasound images from an ultrasound scanner, wherein the plurality of ultrasound images depict at least a portion of the medical device in the in-vitro experimental environment;
   receiving a pre-existing diagram of the probe of the ultrasound scanner;
   determining a four-dimensional model of at least a portion of the medical device being tested in the in-vitro experimental environment based on the received plurality of camera images;
   determining a pose of the probe of the ultrasound scanner based on the pre-existing diagram of the probe and the received plurality of camera images; and
   registering the plurality of ultrasound images with the four-dimensional model based on a common coordinate system of the plurality of camera images and the determined pose of the probe.

2. The method of claim 1, further comprising:
   displaying the four-dimensional model in registration with the plurality of ultrasound images.

3. The method of claim 1, further comprising:
   identifying a region of interest within the four-dimensional model;
   segmenting the region of interest from the four-dimensional model;
   identifying the region of interest within the plurality of ultrasound images;
   segmenting the region of interest within the plurality of ultrasound images; and
   displaying the segmented region of interest within the four-dimensional model in registration with the segmented region of interest from the plurality of ultrasound images.

4. The method of claim 1, further comprising
   calibrating the ultrasound scanner based on the plurality of ultrasound images registered with the four-dimensional model.

5. The method of claim 1, wherein the plurality of cameras are arranged so as to provide a plurality of overlapping views.

6. The method of claim 1, wherein the probe of the ultrasound scanner is rigid.

7. A system for multi-source, multi-type image registration, the system comprising:
   a plurality of image devices;
   a medical imaging device;
   at least one processor; and
   at least one memory including computer program code for one or more programs; the at least one memory and the computer program code configured to, with the at least one processor, cause the system to:
      receive a plurality of images from the plurality of image devices;
      receive a plurality of images from the medical imaging device;
      receive a pre-existing diagram of a probe of the medical imaging device;
      determine a four-dimensional model based on the received plurality of images from the plurality of image devices;
      determine a pose of the probe of the medical imaging device based on the pre-existing diagram of the probe and the received plurality of the images from the plurality of image devices;
      register the plurality of images from the medical imaging device with the four-dimensional model based on a common coordinate system of the image devices and the determined pose of the probe; and
      display the four-dimensional model in registration with the plurality of images from the medical imaging device.

8. The system of claim 7, the at least one memory and the computer program code configured to, with the at least one processor, cause the system to:
   receiving a pre-existing diagram of a probe of the medical imaging device;
   determining a four-dimensional model based on the received plurality of images from the plurality of image devices;
   determining a pose of the probe of the medical imaging device based on the pre-existing diagram of the probe and the received plurality of the images from the plurality of image devices; and
   registering the plurality of images from the medical imaging device with the four-dimensional model based on a common coordinate system of the image devices and the determined pose of the probe.

9. The system of claim 7, the at least one memory and the computer program code configured to, with the at least one processor, cause the system to:
   identify a subject in the four-dimensional model;
   segment the subject from the four-dimensional model;
   identify the subject in the plurality of images from the medical imaging device;
   segment the subject from the plurality of images from the medical imaging device; and
   and wherein the displayed four-dimensional model in registration with plurality of images from the medical imaging device is the segmented subject from the four-dimensional model in registration with the segmented subject from the plurality of images.

10. The system of claim 9, wherein the subject is a physical instrument or an anatomy model.

11. The system of claim 7, the at least one memory and the computer program code configured to, with the at least one processor, cause the system to:
    calibrate the medical imaging device based on the plurality of images registered with the four-dimensional model.

12. The system of claim 7, wherein the plurality of image devices are arranged so as to provide a plurality of overlapping views.

13. The system of claim 7, wherein the plurality of image devices comprise one of a plurality of still cameras, a plurality of video cameras, or a plurality of scanners.

14. The system of claim 7, wherein the medical imaging device comprises an ultrasound scanner or computerized axial tomography scanner.

15. The system of claim 7, wherein the probe of the medical imaging device is rigid.

16. A non-transitory computer readable storage medium having stored therein data representing instructions executable by a programmed processor for multi-source, multi-type image registration, the storage medium comprising instructions for:

receiving a plurality of images from a plurality of image devices;

receiving a plurality of images from a medical imaging device;

receiving a pre-existing diagram of a probe of the medical imaging device;

determining a four-dimensional model based on the received plurality of images from the plurality of image devices;

determining a pose of the probe of the medical imaging device based on the pre-existing diagram of the probe and the received plurality of the images from the plurality of image devices;

registering the plurality of images from the medical imaging device with the four-dimensional model based on a common coordinate system of the image devices and the determined pose of the probe;

identifying a subject in the four-dimensional model;

segmenting the subject from the four-dimensional model;

identifying the subject in the plurality of images from the medical imaging device; and segmenting the subject from the plurality of images from the medical imaging device.

17. The non-transitory computer readable medium of claim 16, further comprising:

displaying the segmented subject from the four-dimensional model in registration with the segmented subject from the plurality of images.

18. The non-transitory computer readable medium of claim 16, further comprising:

calibrating the medical imaging device based on the plurality of images registered with the four-dimensional model.

19. The non-transitory computer readable medium of claim 16, wherein the plurality of image devices are arranged so as to provide a plurality of overlapping views.

20. The non-transitory computer readable medium of claim 16, wherein the plurality of image devices comprise one of a plurality of still cameras, a plurality of video cameras, or a plurality of scanners.

* * * * *